United States Patent [19]
Horvat

[11] Patent Number: 5,824,241
[45] Date of Patent: Oct. 20, 1998

[54] BROMINATED TETRABROMOPHTHALATE ESTER FLAME RETARDANTS FLAME RETARDANT POLYMER COMPOSITIONS

[75] Inventor: Stephen G. Horvat, Solon, Ohio

[73] Assignee: Albemarle Corporation, Richmond, Va.

[21] Appl. No.: 858,757

[22] Filed: May 19, 1997

[51] Int. Cl.[6] .............................. C09K 21/00; C07C 69/76
[52] U.S. Cl. ............................................... 252/609; 560/83
[58] Field of Search .............................. 252/609; 560/83; 524/288

[56] References Cited

U.S. PATENT DOCUMENTS

| | | | |
|---|---|---|---|
| 3,340,226 | 9/1967 | Stivers et al. | 252/609 X |
| 4,375,551 | 3/1983 | Finley | 560/83 |
| 4,631,148 | 12/1986 | Braksmayer et al. | 252/609 |
| 4,762,861 | 8/1988 | Bohen et al. | 521/97 |
| 4,832,873 | 5/1989 | Favstritsky et al. | 252/601 |
| 4,954,542 | 9/1990 | Bohen et al. | 524/89 |
| 5,194,184 | 3/1993 | Takeyama et al. | 252/609 |
| 5,284,604 | 2/1994 | Nishibori et al. | 252/609 |
| 5,302,768 | 4/1994 | Hussain | 570/185 |

FOREIGN PATENT DOCUMENTS 446003   9/1991   European Pat. Off. .

OTHER PUBLICATIONS

Wang, X.K., et al., "Synthesis of Dialkyl Tetrabromophthalates by PTC and Their Flame Retardancy," *Chinese Chemical Letters,* vol. 6, No. 11, pp. 935–938 (1995).

*Primary Examiner*—C. H. Kelly
*Attorney, Agent, or Firm*—E. E. Spielman, Jr.

[57] ABSTRACT

Novel brominated tetrabromophthalate diesters, such as bis(2,3-dibromopropyl) tetrabromophthalate, and flame retardant organic polymer compositions containing such brominated diesters are provided.

10 Claims, No Drawings

BROMINATED TETRABROMOPHTHALATE ESTER FLAME RETARDANTS FLAME RETARDANT POLYMER COMPOSITIONS

This invention relates generally to novel bromine containing organic compounds which are useful as flame retardants, and more specifically to brominated alkyl diesters of tetrabromophthalic anhydride and flame retardant polymer compositions which contain such compounds.

Tetrabromophthalic anhydride is a commercially available reactive intermediate which is useful in making esters, polyesters, polyols and imides which contain aromatic bromine. For example, the diallyl ester of tetrabromophthalic anhydride.

It has now been found that bromination of unsaturated esters of tetrabromophthalic anhydride provides relatively inexpensive, low-volatility, non-blooming flame retardants having a high bromine content and a combination of both aromatic and aliphatic substituted bromine. These flame retardants are especially useful in providing V-2 rated (UL-94 flammability) polypropylene compositions.

In accordance with this invention, there is provided brominated tetrabromophthalate diesters of the formula:

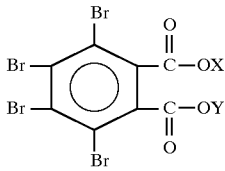

where X and Y are the same or different and have the formula:

where R is a linear or branched chain alkylene radical and each R' is independently either hydrogen or a linear or branched chain alkyl radical.

Also provided is a flame retardant organic polymer composition which comprises an organic polymer and a flame retardant amount of a brominated tetrabromophthalate diester of the formula I above.

The brominated tetrabromophthalate diesters of the invention can be conveniently prepared by the esterification of tetrabromophthalic anhydride (commercially available from Albemarle Corporation as Saytex® RB-49 flame retardant) with an unsaturated species, followed by the bromination of the resulting unsaturated ester.

The preparation of dialkyl esters of tetrabromophthalic anhydride is described, for example, in U.S. Pat. No. 4,375,551 and in Wang et al., "Synthesis of Dialkyl Tetrabromophthalates by PTC and Their Flame Retardancy", *Chinese Chemical Letters*. Vol 6, No. 11, pp 935–938 (1995), which references are both incorporated herein by reference. According to the described process, the anhydride is first reacted with an unsaturated alcohol, which opens the anhydride ring, followed by reacting the resulting monoester intermediate with an unsaturated alkyl halide so as to produce the diester. If the alcohol and alkyl halide contain the same alkyl group structure, the product is a symmetrical diester.

The esters can be prepared from one or more unsaturated alcohols and unsaturated alkyl halides of the formula:

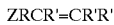

where Z=OH, Br, Cl, or I, R is a linear or branched chain alkylene radical and each R' is independently either hydrogen or a linear or branched chain alkyl radical. Preferably, the R and R' radicals contain from 1 to about 6 carbon atoms. Longer chain radicals could be used but decrease the percentage of bromine in the molecule.

Non-limiting examples of unsaturated alcohols include allyl alcohol, 3-butene-1-ol, 4-pentene-1-ol, 5-hexene-1-ol, 2-methyl-2-propene-1-ol (methallyl alcohol), 3-methyl-3-butene-1-ol, crotyl alcohol and the like. Non-limiting examples of unsaturated alkyl halides include allyl chloride, allyl bromide, 4-bromo-2-methylbutene, 3-bromo-2-methylpropene (methallyl bromide) and the like. Unsymmetrical diesters are prepared using a combination of unsaturated alcohol and unsaturated alkyl halide in which the alkyl group portion of the compounds is different.

The unsaturated diesters can be brominated by any conventional process, such as by adding bromine to an organic solvent solution of the ester. Other brominating agents, such as, for example, benzyltrimethyl ammonium bromide and tetrabutyl ammonium perbromide could be used.

The diesters contain both aromatic and aliphatic substituted bromine and have a high bromine content. For example, bis(2,3-dibromopropyl) tetrabromophthalate has a bromine content of about 73 weight percent. This permits a flame retardant polymer manufacturer to use less flame retardant additive in order to obtain any desired bromine content in the polymer composition. This means that there is less chance of adverse effects on the other properties of the polymer composition due to the presence of the flame retardant. The compounds of the invention also combine the good high temperature processing stability of aromatic substituted bromine compounds with the good flame retardant properties of aliphatic bromine compounds.

Although the brominated esters of the invention can be used to impart flame retardancy to a variety of materials, they are particularly useful with organic polymers, and especially thermoplastic olefin polymers and copolymers such as polyethylene, polypropylene, ethylene-propylene copolymers, polybutylene, polybutadiene, polyisoprene, and the like, including mixtures of such polymers and copolymers.

Non-limiting examples of other polymers useful in the flame retardant organic polymer compositions of the invention include polystyrene, ABS copolymers, styrene-butadiene copolymers, polybutylene terephthalate, polyphenylene ether, polyethylene terephthalate, halogenated resins such as polyvinyl chloride, polyvinyl bromide, polyvinylindene chloride, vinyl chloride-vinyl acetate copolymers, polycarbonate resins, maleic anhydride-styrene copolymers, and the like. The flame retardant diesters of the invention are added to the polymers or copolymers in flame retardant amounts of, for example, from about 1.5 to 12% by weight of the total weight of polymer composition.

The flame retardant compositions can also include compounds which improve their self-extinguishing (SE) properties. For example, antimony, phosphorous and boron containing compounds. Non-limiting specific examples of such SE aids include triphenyl stilbene, trialkoxy stilbine, phosphorous tribromide, phosphorous trichloride, phosphorous oxychloride, triphenyl phosphate, triethyl phosphate, trialkyl borate, and the like. A preferred SE aid is antimony trioxide ($Sb_2O_3$). The SE aids are usually used in amounts of from about 0.5 to 10% by weight of the total weight of polymer composition. Both the flame retardant diesters and the SE aids can be incorporated into a small amount of polymer to form a masterbatch formulation which contains 10 to 50% by weight or more of the additives. The masterbatch is then blended with the bulk of the polymer in amounts to provide the desired percentages of bromine and SE aid in the finished polymer composition.

The polymer compositions can also include conventional additives such as, for example, extrusion aids, acid scavengers, dyes, pigments, fillers, stabilizers, antioxidants, antistatic agents, reinforcing agents, blowing agents, nucleating agents, and the like. The additives are selected and used in amounts to maintain the properties of the finished polymer for its intended utility.

The flame retardant polymer compositions of the invention can be prepared by blending the constituents in any conventional manner. For example, the constituents can first be dry mixed and then fed to a Banbury mixer or an extruder where they are melt blended to form a homogeneous composition.

The invention is further illustrated by, but is not intended to be limited to, the following examples.

EXAMPLE 1

A hazy, white, near solution of 708 g of $CHCl_3$ solvent and 80.87 g(0.157 mole) of diallyl tetrabromophthalate is stirred mechanically with cooling in a 1-liter jacketed flask at 5°–10° C. under nitrogen. To this is added, in 1.5 hours, 50.34 g (0.315 mole, 2.006 ratio of bromine to ester) of bromine, followed by 30 ml of $CHCl_3$. The temperature is maintained at 5°–10° C. during addition. The cooling is turned off after completion of the bromine addition and the reaction mixture is allowed to come to room temperature. The reaction mixture is then stirred for 1 hour at 25° C. and the remaining red color is discharged with about 30–40 ml of 10 wt % aqueous sodium bisulfite and the aqueous phase is separated. A subsequent water wash (200 ml) is acidic. The reaction mixture is then washed with 10 wt % aqueous sodium bicarbonate and the aqueous phase is separated. A subsequent water wash (100 ml) is neutral. Removal of solvent from the organic phase gives a colorless oil which solidifies on standing. The solid product is ground with a mortar and pestle and dried at 35°–45° C. for 1 hour in a vacuum oven to give 117 g of dry product (theory 131 g) which has a melting point by DSC of 80.2°–86.5° C. and a bromine content of 71.7 wt %. From $^1H$ and $^{13}C$ analysis, the product is bis(2,3-dibromopropyl) tetrabromophthalate, Thermogravimetric analysis (TGA) of the product gives the following results:

| Temp °C. | Wt. |
|---|---|
| 50 | 99.99 |
| 100 | 99.91 |
| 150 | 99.89 |
| 200 | 99.85 |
| 250 | 99.62 |
| 300 | 96.87 |
| 350 | 95.08 |
| 400 | 3.14 |
| 450 | 2.88 |
| 500 | 2.56 |
| 550 | 2.24 |
| 600 | 1.99 |

EXAMPLE 2

The bis(2,3-dibromopropyl) tetrabromophthalate flame retardant of Example 1 is blended with two different polypropylenes (Pro-Fax 7523, 4 MFI copolymer and Pro-Fax PD-7196, along with the SE aid, antimony trioxide. Samples of the blends are prepared for physical property, UV stability, and flammability testing. The formulations in weight percent and results are given in Table 1 below.

TABLE 1

| FORMULATION | A | B | C |
|---|---|---|---|
| Pro-Fax 7523 (4MFI copol) | 96.0 | 90.5 | |
| Pro-Fax PD-7194 (18MFI copol) | | | 90.5 |
| Sb203 | 1.0 | 3.2 | 3.2 |
| Flame Retardant | 3.0 | 6.3 | 6.3 |
| PHYSICALS | | | |
| Tensile Yield psi × 1,000 | 3.9 | 3.7 | 3.8 |
| Tensile Modulus psi × 10,000 | 2.1 | 2.0 | 2.1 |
| Elongation, % Yield | 8.7 | 8.3 | 6.8 |
| Flex Strength psi × 1,000 | 5.1 | 5.0 | 5.0 |
| Flex Modulus psi × 10,000 | 1.6 | 1.6 | 1.6 |
| IZOD Impact | 1.67 | 1.74 | 0.7 |
| Gardner Impact in lb/in | 1295 | 1041 | 808 |
| DTUL, ⅛" 66 psi Degrees C. | 78.4 | 76.4 | 83.6 |
| Melt Index, g/10 min 230 Degrees C./2.16 Kg | 4.1 | 4.4 | 21.6 |
| FLAMMABILITY | | | |
| UL-94, ⅛" | V-2 | V-2 | V-2 |
| 1/16" | V-2 | V-2 | V-2 |
| LOI | 24.8 | 26.0 | 25.8 |
| UV Stability | 18.7 | no test | no test |

The UV stability test is a modified ASTM D4459 Xenon arc lamp stability test in which the color of the sample is measured by a calorimeter prior to testing and after exposure to a Xenon arc lamp for 100 hours through filters to simulate long term natural light exposure. A total color change, or Delta E, is then calculated. The more UV stable the sample, the less the Delta E will be.

The UL-94 Underwriters Laboratories standard test is a general test method for plastic flammability and has several sections. The results in Table 1 are obtained from one UL-94 section which is the Vertical burn test. The test provides several UL-ratings as follows:

| | Burn Time (Seconds) | Flaming Drips | Afterglow (Seconds) |
|---|---|---|---|
| V-0 | ≤10 | No | ≤30 |
| V-1 | ≤30 | No | ≤60 |
| V-2 | ≤30 | Yes | ≤60 |
| Burn | ≥30 | Yes/No | >60 |

As indicated in Table I, the samples passed the V-2 rating test.

The oxygen index test (LOI) is a standard ASTM D 2863, ISO 4589-2 test which determines the minimum oxygen content which will support combustion. A larger LOI indicates lower flammability.

The compounds of the invention can be easily and economically prepared and contain high bromine contents of about 70% or more, with both aliphatic and aromatic bromine. Accordingly, they are stable at polymer processing temperatures with a minimum impact on polymer properties while providing satisfactory flame retardancy for many applications. They are also expected to be non-blooming, in part, due to functional and structural characteristics which are analogous to two brominated flame retardants with demonstrated non-blooming characteristics, ethylene bis dibromonorbornane dicarboxamide and ethylene bis tetrabromophthalimide.

What is claimed is:

1. A brominated tetrabromophthalate diester of the formula:

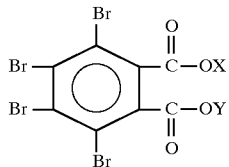

where X and Y are the same or different and have the formula:

RCR'BrCR'R'Br where R is a linear or branched chain alkylene radical and each R' is independently either hydrogen or a linear or branched chain alkyl radical.

2. A brominated tetrabromophthalate diester according to claim 1 wherein X and Y are the same.

3. A brominated tetrabromophthalate diester according to claim 1 where R contains from 1 to about 6 carbons and R' is hydrogen or an alkyl radical which contains from 1 to about 6 carbons.

4. A brominated tetrabromophthalate diester according to claim 2 which is bis(2,3-dibromopropyl) tetrabromophthalate.

5. A brominated tetrabromophthalate diester according to claim 1 wherein X and Y are different.

6. A flame retardant organic polymer composition comprising an organic polymer and a flame retardant amount of a brominated diester of the formula:

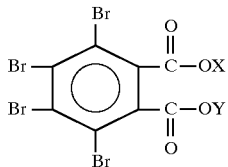

where X and Y are the same or different and have the formula:

RCR'BrCR'R'Br where R is a linear or branched chain alkylene radical and each R' is independently either hydrogen or a linear or branched chain alkyl radical.

7. The composition according to claim 6 wherein said organic polymer is an olefinic polymer.

8. The composition according to claim 7 wherein said polymer is a polypropylene polymer and said brominated diester is bis(2,3-dibromopropyl) tetrabromophthalate.

9. The composition according to claim 6 wherein said composition includes a self-extinguishing aid.

10. The composition according to claim 9 wherein said self-extinguishing aid is antimony trioxide.

* * * * *